United States Patent [19]

Cheo

[11] 4,363,966

[45] Dec. 14, 1982

[54] DETECTION SYSTEM FOR DISTINGUISHING BETWEEN VOIDS AND FOREIGN PARTICLES IN MATERIALS AND METHOD

[75] Inventor: Peter K. Cheo, West Hartford, Conn.

[73] Assignee: Electric Power Research Institute, Inc., Palo Alto, Calif.

[21] Appl. No.: 189,025

[22] Filed: Sep. 22, 1980

[51] Int. Cl.³ .............................................. G01J 1/00
[52] U.S. Cl. .................................. 250/339; 250/341; 356/239
[58] Field of Search ....................... 250/339, 341, 349; 356/239, 51

[56] References Cited

U.S. PATENT DOCUMENTS

| 3,405,270 | 10/1968 | Briggs ................................. 258/341 |
| 3,693,025 | 9/1972 | Brunton ........................... 250/339 X |
| 3,870,884 | 3/1975 | Williams ............................... 250/339 |
| 4,197,457 | 4/1980 | Cheo ..................................... 250/339 |
| 4,208,126 | 6/1980 | Cheo et al. ............................. 356/51 |

Primary Examiner—Davis L. Willis
Attorney, Agent, or Firm—Flehr, Hohbach, Test, Albritton & Herbert

[57] ABSTRACT

A technique which detects for the presence of particles or voids in material is disclosed herein. This technique utilizes an overall optics arrangement for producing a beam of radiation and for directing the latter into and through the material such that any void or foreign particle which is present causes the radiation impinging thereon to form an overall scattering pattern distinctly characteristic of whether the impinged void or foreign particle is generally spherical or non-spherical in shape. The technique disclosed herein also provides an arrangement for detecting scattered radiation, if any, and distinguishing between spherical and non-spherical foreign particles and, in a preferred embodiment, whether the impinged void/foreign particle is relatively large or small, relative to wavelength of said beam.

12 Claims, 7 Drawing Figures

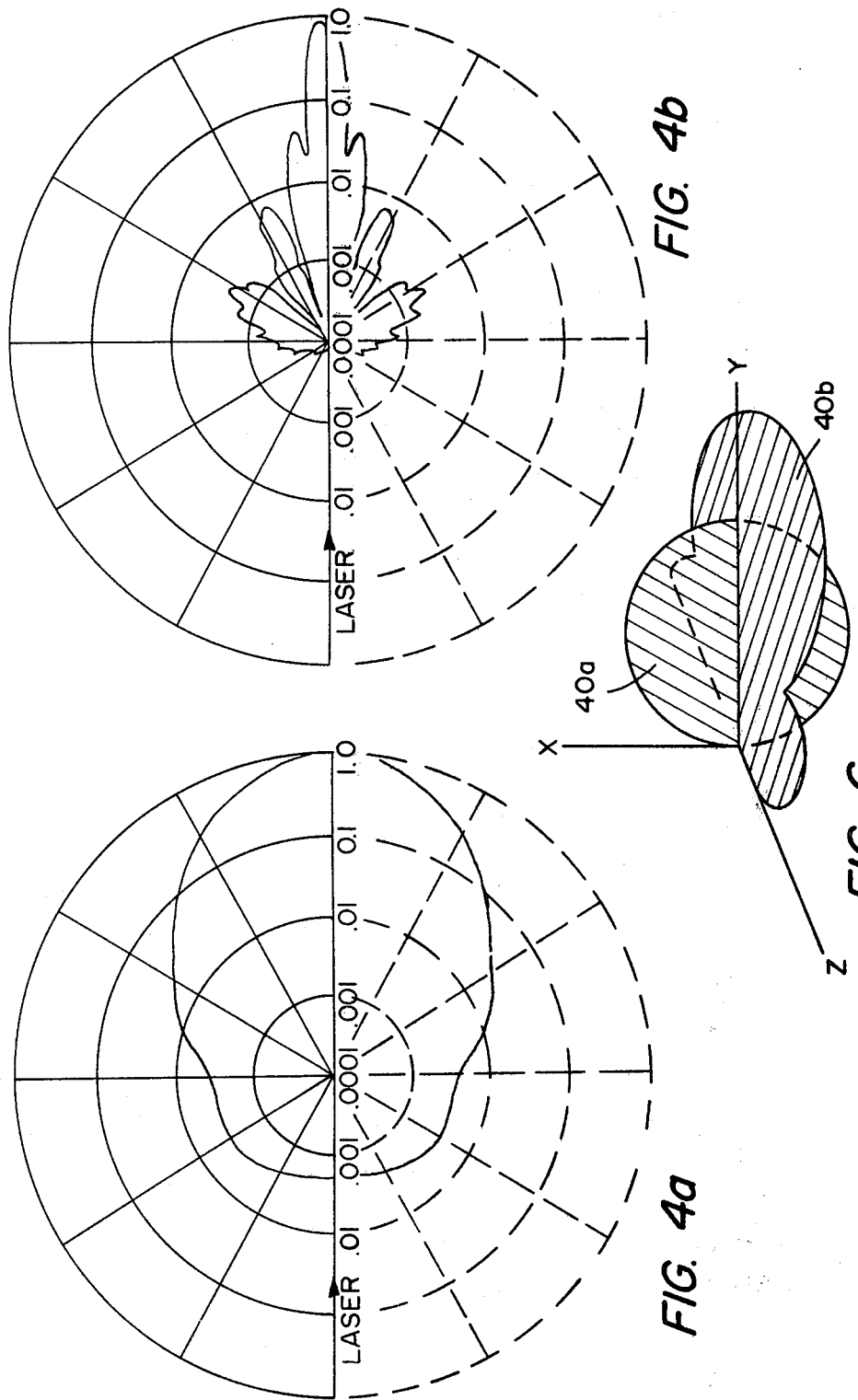

DETECTION SYSTEM FOR DISTINGUISHING BETWEEN VOIDS AND FOREIGN PARTICLES IN MATERIALS AND METHOD

The present invention relates generally to a technique for detecting the presence of particles or voids in a given material and more particularly to an improvement in the detection techniques disclosed in U.S. Pat. No. 4,197,457 (Cheo) and in U.S. patent application Ser. No. 909,254, filed May 24, 1978 and entitled SYSTEM FOR DETECTING FOREIGN PARTICLES OR VOIDS IN ELECTRICAL CABLE INSTALLATION AND METHOD (Cheo et al.), both of which have been assigned to the assignee of the present application.

In the above recited Cheo patent, a technique for the detection of voids or foreign particles in a material such as polyethylene, polyvinylchoride or any far infrared (FIR) transparent media is disclosed. This technique uses suitable means for producing a laser beam of electromagnetic radiation at a wavelength within the FIR range and directing this beam into the material being monitored along a particular path incident thereto. In this way, any portion of the beam which passes through the material unobstructed by voids or foreign matter does so along predictable non-impinging paths through the material and any portion of the beam which impinges the foreign particle or void is scattered by the latter along predictable scatter paths. Means are provided for detecting the scattered radiation and thereby detecting the presence of a void or foreign particle. In the Cheo et al. application, a specific index matching arrangement is disposed around the material being monitored in order to better control the way in which the laser beam enters and leaves the material. While the techniques disclosed in the Cheo patent and the Cheo et al. application are satisfactory for their intended purpose, that is, to detect voids or foreign particles in certain materials, they are not capable of accurately distinguishing between spherical and non-spherical voids or particles. This latter capability is important because it can aid in determining the origin of these defects and thereby to commence the necessary steps to correct the manufacturing processing in order to eliminate further re-occurence. Therefore, this additional capability would be a significant improvement over either the Cheo patent or the Cheo et al. patent application.

In view of the foregoing, a primary object of the present invention is to provide a particular technique for detecting the presence of particles or voids in a material and specifically to a technique which is capable of distinguishing between spherical voids and foreign particles of irregular shape in an uncomplicated way.

Another object of the present invention is to provide a particle/void detection technique which is capable of distinguishing between relatively large and small particles/voids and whether the defect detected is a void or solid particle.

A more particular object of the present invention is to provide an improved detection arrangement which is especially suitable for use in the Cheo patent and Cheo et al. patent application recited above.

As will be discussed in detail hereinafter, the system (and its method of operation) disclosed herein is one which utilizes a beam of radiation, preferably a far infrared laser beam of electromagnetic radiation as in the Cheo patent and the Cheo et al. patent application recited above. This beam is directed into the material being monitored along a predetermined path incident to the material such that (1) any portion of the beam which passes through the material unobstructed by voids or foreign particles does so along predictable non-impinging paths and (2) any portion of the beam which impinges one of the voids or particles forms an overall scattering pattern which is distinctly characteristic of whether the impinged void or foreign particle is generally spherical or non-spherical in shape. In accordance with the present invention, means are provided for detecting the scattered radiation, if any, in a way which distinguishes between a spherical or non-spherical void/foreign particle. This is carried out by the use of a number of independent detectors which are placed in predetermined locations based on known scattering patterns for both spherical and non-spherical particles and voids.

The system and its method of operation disclosed herein will be described in more detail hereinafter in conjunction with the drawings wherein:

FIG. 4a is a two dimensional graphic illustration of the scattering pattern resulting from electromagnetic radiation impinging upon a relatively small spherical particle/void located in the coordinate system of FIG. 3;

FIG. 4b is a graphic illustration similar to FIG. 4a illustrating a scattering pattern resulting from electromagnetic radiation impinging on a much larger, spherical/void in the same coordinate system;

FIG. 6 is a three dimensional diagrammatic illustration of the scattering pattern resulting from electromagnetic radiation impinging on the non-spherical particle/void illustrated in FIG. 5, as shown in the x, y, z coordinate system.

Figure 1:
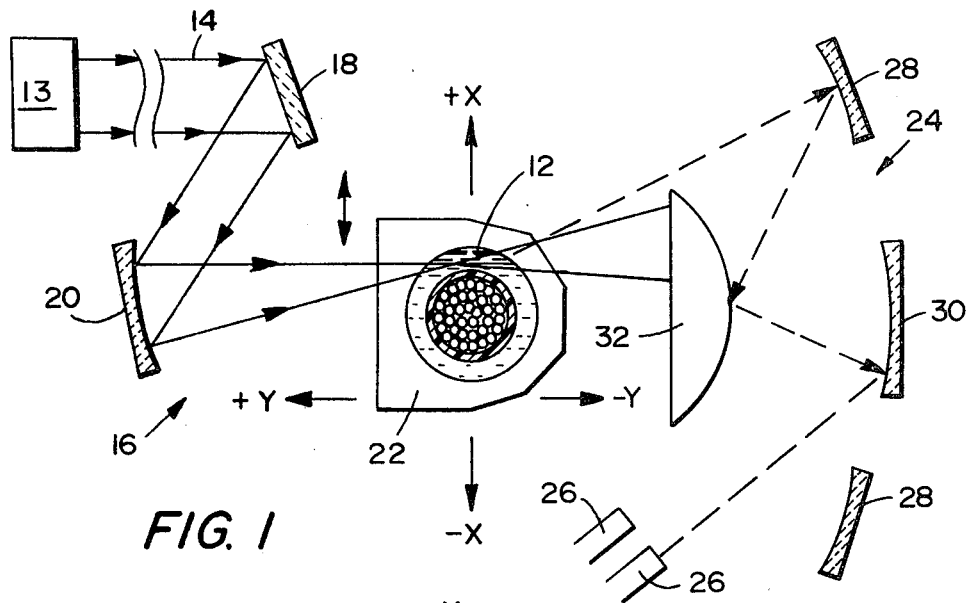
FIG. 1 is a diagrammatic illustration of a system which is provided for detecting particles and voids in specific material but which does not include a detection arrangement designed to distinguish between spherical and non-spherical particles/voids.

Turning now to the drawings, attention is first directed to FIG. 1 which diagrammatically illustrates a system 10 for detecting the presence of particles or voids in a material, specifically plastic cable insulation 12 forming part of an overall cable. System 10 is one which is described in an Electric Power Research Institute ("EPRI") publication entitled LASER DETECTION OF VOIDS AND CONTAMINANTS IN POLYETHYLENE-INSULATED POWER CABLE, EPRO EL-1266, project 794-2, final report Dec. 1979. Reference is made to this report which disclosed as part of system 10 a laser apparatus for producing an FIR laser beam 14, e.g., one within the FIR range of about 70 microns and 2000 microns, specifically one having a wavelength of 119 micrometers. An optical arrangement generally designated by the reference numeral 16 is provided for directing the beam into insulation layer 12 along a path incident to the insulation in a predetermined scanning fashion. As shown in FIG. 1, arrangement 16 includes a number of optical components including a scanning mirror 18 and a focusing mirror 20.

An index matching arrangement 22 is provided around the section of insulation 12 being monitored and, in a preferred embodiment, is of the type described in the previously recited Cheo et al. patent application. As the electromagnetic radiation from beam 14 passes through insulation layer 12, any portion thereof which passes through the material unobstructed by the foreign particles or voids will do so along predictable non-impinging paths through the material. On the other hand, the portion of the beam which impinges on the foreign particle or void as it passes through the material will be scattered thereby along predictable scatter paths different than the non-impinging paths. This is described in the above recited Cheo patent and the Cheo et al. application. In order to detect for a particle or void, system 10 includes an arrangement 24 which detects for the scattered radiation. As seen in FIG. 1, this arrangement includes a series of detectors 26 and optical components, specifically two collecting mirrors 28, a field mirror 30 and a blocking mirror 32 located in predetermined positions relative to the section of insulation material being monitored for detecting the scattered radiation, if any, and thereby the presence or absence of a particle or void.

System 10 briefly discussed above is described in more detail in the previously recited EPRI publication in combination with the Cheo patent and Cheo et al. patent application. While this system is satisfactory for its intended purpose, it is not designed to distinguish between the presence of spherical and non-spherical particles or voids in cable insulation 12. However, as will be described hereinafter, by replacing arrangement 24 with an arrangement 32 of detectors 34 illustrated in FIG. 2, system 10 is capable of distinguishing between spherical and non-spherical particles/voids. As will also be seen hereinafter, by utilizing arrangement 32, which is designed in accordance with the present invention and which will be discussed in detail below, system 10 is also capable of distinguishing between relatively large particles/voids and whether or not it is a solid particle or void which has been detected.

Before discussing arrangement 32 in detail, it is important to emphasize that the other components making up system 10 do not form part of the present invention other than as necessary components in the overall system and hence will not be described in detail, particularly since they have been described in the Cheo patent, the Cheo et al. application and/or the EPRI publication. Moreover, as will be apparent hereinafter, arrangement 32 could be used with an overall detection system other than system 10, that is, the various other components of system 10 could vary from the manner described in these references so long as the variations are compatible with arrangement 10. For example, as will be seen, it is not necessary for the beam 14 to be an FIR beam and the system does not necessarily have to use an index matching arrangement 22 of the type described in the Cheo et al. patent application. In fact, arrangement 32 may be applicable in systems for detecting particles/voids in material other than cable insulation, for example tires, and material which does not require any index matching arrangement at all.

Figure 3:
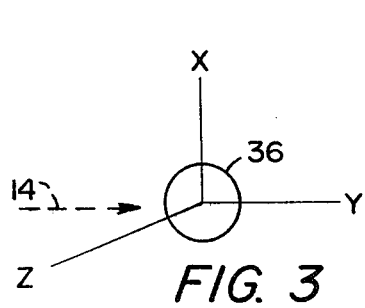
FIG. 3 is a diagrammatic illustration of a spherical particle located at the origin of an x, y, z coordinate system.

Referring to FIG. 3, attention is directed to a spherical particle or void 36 which, for illustrative purposes, is shown at the origin of an x, y, z coordinate system. FIGS. 4a and 4b graphically illustrate in two dimensions (the xy plane) the scattering patterns resulting from the impingement of particle/void 36 by FIR beam 14. As seen in FIG. 3, the beam is indicated by dotted lines and impinges the particle/void from the left to the right along the y-axis. In the case of FIG. 4a, spherical particle/void 36 is relatively small, having a diameter comparable to one wavelength of the light, $\lambda$, and FIG. 4b is characteristic of a larger sphere, specifically one having a diameter comparable to six times the wavelength ($6\lambda$). It has been found that the scattered laser radiation pattern of spherical particles/voids, both large and small, displays a spherical symmetry with respect to the forward laser beam direction. This symmetry in the xy plane is apparent in both FIGS. 4a and 4b. While not shown, this symmetry also exists entirely around the y-axis.

While the scattering patterns illustrated in FIGS. 4a and 4b are both symmetical, it should be apparent that their planar configurations are very different from one another. In FIG. 4a the planar configuration of the scattering pattern is almost circular, that is, the intensity of the scattered radiation along the curve changes slowly. This has been found to be characteristic of small spherical particle/voids, e.g. ones having diameters equal to or less than the wavelength ($\lambda$) of the impinging beam. On the other hand, the intensity along the curve in FIG. 4b changes quite rapidly which has been found to be characteristic of larger spherical particles/voids, for example those having a diameter equal to or greater than $3\lambda$ of the impinging beam.

By analyzing a non-spherical particle/void, specifically a semi-conducting particle (carbon black material) embedded in cross-linked polyethylene insulation, it has been found that symmetry of its scattering pattern is not preserved. In this case, the non-spherical material was elongated, somewhat rod-like, having a cross-sectional diameter of approximately 3 mils and a length of 15 mils. This is best exemplified in general by means of the rod shaped particle 38 illustrated in FIG. 5. As shown there, the particle extends along the z-axis in an x, y, z coordinate system with its center at the origin thereof. FIG. 6 illustrates the expected scattering pattern resulting from the impingement of the particle by beam 14. The beam is shown impinging the particle from left to right along the y-axis in FIG. 5. The scattering patterns illustrated in FIG. 6 are those in the xy plane and the yz plane. For purposes of reference, these patterns are generally designated by the reference numerals 40a and 40b, respectively.

At the outset, it should be apparent that these patterns are different from one another and that they are not symmetrical about the y-axis. The scattering pattern 40a is somewhat isotropic, that is, similar to the scattering pattern illustrated in FIG. 4a. This is because the cross-section of particle 38 is circular and also small, e.g., 3 mils. If the cross-section were large, for example on the order of 15 mils, the scattering pattern 40a would be similar to the pattern illustrated in FIG. 4b. On the other hand, the scattering pattern 40b resembles a cloverleaf in configuration having an outermost section which is elongated along the y-axis. The scattering pattern between section 40a and 40b will vary between these two configurations and eventually merge at points therebetween.

As will be seen hereinafter, the expected scattering patterns illustrated in FIGS. 4a and 4b and 6 form the basis for operation of arrangement 32 so as to distinguish between spherical and non-spherical particles/voids, between relatively small and relatively large particles/voids and between defects which are solid particles or voids. In this regard, it is to be understood that arrangement 32 serves only to provide a fundamental guide-line for estimating the characteristics of the scatterers. If the particle or void detected is clearly a sphere and it is centrally oriented with respect to the incoming beam, as in FIG. 3, arrangement 32 will accurately indicate its spherical shape. In the same manner if the particle/void is rod-shaped and oriented in the manner shown in FIG. 5 with respect to the incoming beam, arrangement 32 will indicate its non-spherical shape. However, if the particle/void is not spherical and not rod-shaped but somewhere therebetween, for example oval and/or if the particle/void is not positioned as in FIG. 3 or 5 with respect to the incoming beam, the scattering pattern resulting therefrom will vary from the patterns shown in FIGS. 4a, 4b and 6. As a result, the results from arrangement 32 will become more of an approximation as to shape and size of the detected particle/void.

Figure 2:
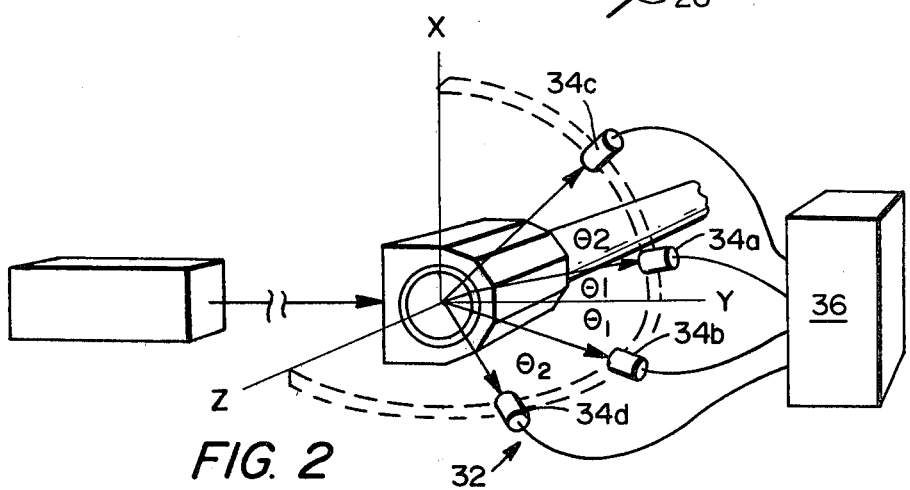
FIG. 2 is a diagrammatic illustration of a detection arrangement for distinguishing between spherical and non-spherical particles/voids and specifically an arrangement which is suitable for use in the system shown in FIG. 1 or those in the Cheo patent and the Cheo et al. patent application.
Figure 5:
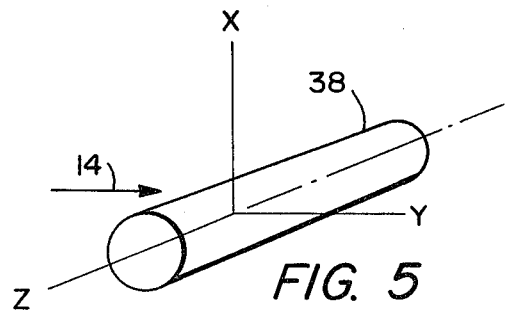
FIG. 5 is a diagrammatic illustration of a non-spherical particle/void located at the origin of an x, y, z coordinate system.

Returning to FIG. 2, the arrangement 32 of detectors 34 are shown within the same x, y, z coordinate system as the particle/voids 36 and 38 and the particle/void being detected in FIG. 3 is assumed to be located at the origin of the coordinate system with the beam impinging on the particle/void from the left to the right along the y-axis as in FIGS. 3 and 5. For purposes of description, the four detectors 34 will be differentiated from one another by the letters a, b, c and d. Each of these detectors may be identical to the others and each may be as described in the Cheo patent, Cheo et al. application and/or the EPRI publication recited above. All of the detectors are equidistant from the origin of the coordinate system. As seen in FIG. 2, the detectors 34a is located in the xy plane at an angle $\theta_1$ about the y-axis. The detector 34b is located in the yz plane at the same angle as $\theta_1$ from the y-axis. Detector 34c is located in the xy plane at a greater angle from the y-axis as indicated by the angle $\theta_2$. Finally, detector 34d is located in the yz plane at the same angle $\theta_2$ from the y-axis as detector 34c. In a preferred embodiment $\theta_1$ is 15° and $\theta_2$ is 25°. All of the detectors are connected to suitable processing circuitry 36 which will be discussed hereinafter.

For purposes of describing how the detectors 34 distinguish between spherical and non-spherical particles and voids and whether or not the particles/voids are relatively large or small, it will be assumed that the particle/void detected is located at the origin of the coordinate system. It will also be assumed initially that the particle/void is spherical and small, e.g. having a diameter equal to or less than the wavelength of the incoming beam. Under these latter conditions, the scattering pattern illustrated in FIG. 4a will result. Therefore, the intensity at detectors 34a and 34b will be approximately equal to one another and therefore the signals they produce will be approximately equal. Similarly, the intensity at detectors 34c and 34d and their output signals will be approximately equal. These pairs of approximately equivalent signals will thereby indicate that the particle/void detected is spherical or approximately spherical in shape. Moreover, because the particle/void is small, the difference in intensity at the detectors 34a and 34c or 34b and 34d is small (again see FIG. 4a), resulting in signal differences which are small. If the spherical particle detected were large, for example having a diameter approximately equal to or greater than 3λ, the difference in intensity at the detectors 34a and 34c or 34b and 34d would be relatively large (see FIG. 4b) resulting in a relatively large signal difference. The measured signal difference is an accurate estimate of the diameter of the particle/void.

Assuming now that the particle/void detected is rod-shaped and located at the center of the coordinate system as shown in FIG. 5, the scattering pattern would be similar to the one illustrated in FIG. 6. Therefore, the intensity at detectors 34a and 34b would be significantly different and therefore their output signals would be significantly different. This is also true for the detectors 34c and 34d. Because of the circular nature of the cross-section of the particle/void, its diameter can be estimated to be the difference between the output signals from detectors 34a and 34c or 34b and 34d in the same manner as spherical particle/void.

As stated above, the output signals from detectors 34 can be applied to processing circuitry 36 which comprises part of the overall detection arrangement 32. Circuitry 36 can be readily provided to act on the signals for providing a visual or printed readout indicating whether the particular void detected is spherical or non-spherical and whether or not it is small or large relative to the wave length of beam 14. As a general rule, when arrangement 32 indicates that a detected particle/void is spherical, the defect detected is usually a void by virtue of its spherical shape. However, this is not always true and therefore arrangement 32 may include other means to distinguish between voids and particles. Specifically, at least one detector 34e is located in front of the material being monitored, that is, to the left of the xz plane as viewed in FIG. 2. This detector is used to detect any back scattering radiation from the particle or void detected. In this regard, back scattered radiation resulting from solid particles is usually greater in intensity than back scattering radiation from voids since most of the radiation impinging on a void passes therethrough in the forward direction. Therefore, relatively large signals provided at the output of detector 34a will generally be construed to mean a solid particle has been detected and relatively small signals will generally be construed to mean that a void has been detected, especially if the defect detected is spherical.

As stated previously, arrangement 32 serves only to estimate whether a particle or void is detected, whether it is spherical or non-spherical and whether it is relatively large or small. The reliability of this estimate may be increased by increasing the field of coverage. Specifically, a second group of detectors 34a, b, c and d would be provided. These second detectors could be positioned relative to one another in the same way as the first group with the second group oriented at an angle of rotation about the y-axis with respect to the first group, for example 90°. Additional groups could be provided between these first two groups. In this way, the overall arrangement of detectors becomes less sensitive to the orientation of the defect within the coordinate system. By processing all of the signals from all of these detectors, the processing circuitry can determine whether the particle/void is spherical or non-spherical, its relative size and its orientation in the x, y, z coordinate system. This could also be accomplished by using a single group of detectors, e.g. the detectors illustrated in FIG. 2 and rotating this group about the y-axis while simultaneously taking readings. In this regard, whether a single group of detectors 34a–d or a number of groups are used, the number of detectors in each group is not limited to the four disclosed but could include a greater even number so as to provide more than two pairs in each group.

It is claimed:

1. A system for detecting the presence of particles or voids in a materials of a specific type capable of passing a particular beam of radiation therethrough, said system comprising:
   (a) means for producing said beam of radiation;
   (b) means for directing said beam into said material along a predetermined path incident to said material such that
      (i) any portion of said beam which passes through said material unobstructed by voids or foreign particles within said material does so along predictable non-impinging paths, and
      (ii) any portion of said beam which impinges one of said voids or foreign particles as it passes through said material is scattered thereby along scattering paths which define an overall scattering pattern distinctly characteristic of whether the impinged void or foreign particle is generally spherical or non-spherical in shape; and
   (c) means for detecting said scattered radiation, if any, and distinguishing between whether the impinged upon void or foreign particle is generally spherical or non-spherical in shape.

2. A system according to claim 1 wherein said scattering pattern is distintly characteristic of whether the impinged void or particle is relatively large or small in comparison with the wavelength of said beam and wherein said detecting means distinguishes between said relatively larger and smaller voids or particles.

3. A system according to claim 2 wherein said scattering pattern is distinctly characteristic of whether a void or a solid foreign particle is impinged upon and wherein said detecting means includes means for distinguishing between said void and solid particle.

4. A system according to claim 1 wherein said detecting means includes means detecting for said scattered radiation at least at four distinct points behind said material relative to said incident path.

5. A system according to claim 4 wherein said four distinct points of detection are equidistant from said material and include:
   (a) first and second points respectively located in intersecting perpendicular planes, each of which includes said incident beam path, said first and second points being equidistant from the line of intersection of said planes, and
   (b) third and fourth points respectively located in said planes equidistant from said intersection line but further from the latter than said first and second points.

6. A system according to claim 5 wherein said detecting means includes means detecting for said scattered radiation at a fifth point in front of said material.

7. A system according to claim 1 wherein said beam of radiation is at a given wavelength within the far infrared range of about 70 microns to 2000 microns and wherein said material is one having characteristics including a known absorption coefficient and a known index of refraction such that said material is substantially transparent to radiation at said given wavelength.

8. A system for detecting the presence of particles or voids in material of the type which is substantially transparent to radiation at a given wavelength in the far infrared range of about 70 microns to about 2000 microns, said system comprising:
   (a) means for producing a laser beam of electromagnetic radiation at said given wavelength;
   (b) means for directing said beam into said material along a predetermined path incident to said material such that
      (i) any portion of said beam which passes through said material unobstructed by voids or foreign particles within said material does so along predictable non-impinging paths, and
      (ii) any portion of said beam which impinges one of said voids or foreign particles as it passes through said material is scattered thereby along scattering paths which define an overall scattering pattern distinctly characteristic of whether the impinged void or foreign particle is generally spherical or non-spherical in shape; and
   (c) a detection arrangement for detecting said scattered radiation, if any, and distinguishing between whether the impinged upon void or particle is generally spherical or non-spherical and whether or not it is a relatively large or small particle relative to wave length of said beam, said detection arrangement including means detecting for scattered radiation at least at four distinct points behind said material relative to said incident path and equidistant from said material, said four points including
      (i) first and second points respectively located in intersecting perpendicular planes, each of which includes said incident path, said first and second points being equidistant from the line of intersection of said planes, and
      (ii) third and fourth points respectively located in said planes equidistant from said intersection line but further from the latter than said first and second points.

9. A method of detecting the presence of particles or voids in a material of a specific type capable of passing a particular beam of radiation therethrough, said method comprising:
   (a) producing said beam of radiation;
   (b) directing said beam into said material along a predetermined path incident to said material such that
      (i) any portion of said beam which passes through said material unobstructed by voids or foreign particles within said material does so along predictable non-impinging paths, and
      (ii) any portion of said beam which impinges one of said voids or foreign particles as it passes through said material is scattered thereby along scattering paths which define an overall scattering pattern distinctly characteristic of whether the impinged void or foreign particle is generally spherical or non-spherical in shape; and
   (c) detecting said scattered radiation, if any, and distinguishing between whether the impinged upon void or foreign particle is generally spherical or non-spherical in shape.

10. A method according to claim 9 wherein said scattering pattern is distinctly characteristic of whether the impinged void or particle is relatively large or small relative to the wavelength of said beam and wherein said detecting step distinguishes between said relatively larger and smaller voids or particles.

11. A method according to claim 10 wherein said scattering pattern is distinctly characteristic of whether a void or a solid foreign particle is impinged upon and wherein said detecting step distinguishes between said void and solid particle.

12. A method of detecting the presence of particles or voids in material of the type which is substantially transparent to radiation at a given wavelength in the far infrared range of about 70 microns to about 2000 microns, said method comprising:
  (a) producing a laser beam of electromagnetic radiation at said given wavelength;
  (b) directing said beam into said material along a predetermined path incident to said material such that
    (i) any portion of said beam which passes through said material unobstructed by voids of foreign particles within said material does so along predictable non-impinging paths, and
    (ii) any portion of said beam which impinges one of said voids or foreign particles as it passes through said material is scattered thereby along scattering paths which define an overall scattering pattern distinctly characteristic of whether the impinged void or foreign particle is generally spherical or non-spherical in shape; and
  (c) detecting said scattered radiation, if any, and distinguishing between whether the impinged upon void or particle is generally spherical or non-spherical and whether or not it is a relatively large or small particle, said detection step including detecting for scattered radiation at least at four distinct point behind said material relative to said incident path and equidistant from said material, said four points including
    (i) first and second points respectively located in intersecting perpendicular planes, each of which includes said incident path, said first and second points being equidistant from the line of intersection of said planes, and
    (ii) third and fourth points respectively located in said planes equidistant from said intersection line but further from the latter than said first and second points.

* * * * *